United States Patent [19]

Ross et al.

[11] Patent Number: 5,874,631
[45] Date of Patent: Feb. 23, 1999

[54] METHOD AND COMPOSITION TO INCREASE THE LIFE OF LIQUID HYDROXY-AND ALKOXYALKYL KETONES

[75] Inventors: Karl-Heinz Ross, Grünstadt; Ludwig Wambach, Schwetzingen; Harro Wache, Fussgönheim, all of Germany

[73] Assignee: BASF Aktiengesellschaft, Ludwigshafen, Germany

[21] Appl. No.: 716,599

[22] Filed: Sep. 18, 1996

[30] Foreign Application Priority Data

Sep. 23, 1995 [DE] Germany .......................... 19535404.4

[51] Int. Cl.6 .................................................. C07C 45/86
[52] U.S. Cl. ............................................ 568/304; 568/421
[58] Field of Search ..................... 568/304, 421

[56] References Cited

U.S. PATENT DOCUMENTS 2,294,286   8/1942   Dannenberg et al. ................. 568/304
2,444,006   6/1948   Dannenberg ........................... 568/304

FOREIGN PATENT DOCUMENTS 326397   8/1984   European Pat. Off. ............... 568/304
206777   2/1984   Germany ............................... 568/304
641443   8/1950   United Kingdom .................. 568/304

OTHER PUBLICATIONS

Chem. Abstracts 88:74049n (1978), Miyamoto et al (JP 52 116 407).

Primary Examiner—James H. Reamer
Attorney, Agent, or Firm—John H. Shurtleff

[57] ABSTRACT

A method for increasing the shelf life of liquid hydroxy- and alkoxyalkyl ketones by adding from 0.0001 to 1% by weight of a base is described.

17 Claims, No Drawings

METHOD AND COMPOSITION TO INCREASE THE LIFE OF LIQUID HYDROXY-AND ALKOXYALKYL KETONES

The present invention relates to a method for increasing the shelf life of liquid hydroxy- and alkoxyalkyl ketones by addition of small amounts of a base.

Liquid hydroxy- and alkoxyalkyl ketones, e.g. hydroxyacetone, are prone to side reactions on storage. As a result the content of the stored goods decreases, and they thereby become contaminated and in some cases discolor.

It is an object of the present invention to remedy the abovementioned disadvantages.

We have found that this object is achieved by a novel method for increasing the shelf life of liquid hydroxy- and alkoxyalkyl ketones, which comprises adding from 0.0001 to 1% by weight of a base.

Suitable hydroxyalkyl ketones are hydroxyacetone, 1-hydroxy-butane-2-one or mixtures thereof, preferably hydroxyacetone.

Suitable alkoxyalkyl ketones are methoxy-2-propanone, ethoxy-2-propanone, n-propoxy-2-propanone, isopropoxy-2-propanone, n-butoxy-2-propanone, isobutoxy-2-propanone, sec-butoxy-2-propanone, tert-butoxy-2-propanone, methoxy-2-butanone, ethoxy-2-butanone, n-propoxy-2-butanone, isopropoxy-2-butanone, n-butoxy-2-butanone, isobutoxy-2-butanone, sec-butoxy-2-butanone, tert-butoxy-2-butanone, 1-methoxy-butan-3-one, 1-ethoxy-butan-3-one, 1-methoxy-1-buten-3-one, ethoxy-1-buten-3-one or mixtures thereof, preferably methoxy-2-propanone, ethoxy-2-propanone, n-propoxy-2-propanone, methoxy-2-butanone, ethoxy-2-butanone, n-propoxy-2-butanone or mixtures thereof, particularly preferable methoxy-2-propanone and methoxy-2-butanone.

From 0.0001 to 1% by weight, preferably from 0.001 to 0.1% by weight, particularly preferably from 0.005 to 0.05% by weight, of a base are generally added to the liquid hydroxy- and alkoxyalkyl ketones to be stabilized.

Suitable bases are tertiary amines, preferably tertiary alkylamines, particularly preferably trialkylamines such as trimethylamine, dimethylethylamine, methyldiethylamine, triethylamine, tri-n-propylamine, triisopropylamine or tetramethylethanediamine, tetramethyl-n-propanediamine, tetramethyl-n-butanediamine, tetramethyl-n-pentanediamine, tetramethyl-n-hexanediamine or solid or aqueous solutions of alkali metal hyrdoxides, alkali metal carbonates, alkali metal hydrogen carbonates, alkaline earth metal hydroxides, alkaline earth metal carbonates and alkaline earth metal hydrogen carbonates such as lithium hydroxide, sodium hydroxide, potassium hydroxide, calcium hydroxide, magnesium hydroxide, lithium carbonate, sodium carbonate, potassium carbonate, calcium carbonate, magnesium carbonate, lithium hydrogen carbonate, sodium hydrogen carbonate, potassium hydrogen carbonate, calcium hydrogen carbonate, magnesium hydrogen carbonate or mixtures thereof, preferably sodium hydroxide, potassium hydroxide, sodium carbonate, potassium carbonate or mixtures thereof.

EXAMPLES

Comparison Example A 200 ml of freshly distilled hydroxyacetone were stored at room temperature (25° C.). The results are summarized in Table A.

TABLE A

Unstabilized hydroxyacetone

| Weeks | Content [% by weight] |
|---|---|
| 0 | 97.8 |
| 3 | 91.8 |
| 7 | 91.3 |

Example 1

200 ml of freshly distilled hydroxyacetone were treated with N,N,N',N'-tetramethylhexanediamine (TMHDA) such that the content was 100 ppm. The results are summarized in Table 1.

TABLE 1 hydroxyacetone stabilized with 100 ppm of N,N,N',N'-tetramethylhexanediamine

| Weeks | Content [% by weight] without TMHDA | Content [% by weight] with 100 ppm of TMHDA |
|---|---|---|
| 0 | 97.8 | 97.8 |
| 3 | 91.8 | 97.8 |
| 7 | 91.3 | 97.6 |
| 9 | — | 97 |

Example 2

200 ml of freshly distilled hydroxyacetone were treated with N,N,N',N'-tetramethylhexanediamine such that the content was 250 ppm. The results are summarized in Table 2.

TABLE 2 hydroxyacetone stabilized with 250 ppm of N,N,N',N'-tetramethylhexanediamine

| Weeks | Content [% by weight] without TMHDA | Content [% by weight] with 250 ppm of TMHDA |
|---|---|---|
| 0 | 97.8 | 97.8 |
| 3 | 91.8 | 97.8 |
| 7 | 91.3 | 97.6 |
| 9 | — | 97.6 |

Examples 3 and 4

200 ml of freshly distilled hydroxyacetone were treated with a 25% strength aqueous sodium carbonate solution such that the content of sodium carbonate was 300 ppm. In a further experiment, the conntent was adjusted to 100 ppm of sodium carbonate. The results are summarized in Table 3.

TABLE 3 hydroxyacetone stabilized with sodium carbonate

| Weeks | Content [% by weight] without sodium carbonate | Content [% by weight] with 100 ppm of sodium carbonate | Content [% by weight] with 250 ppm of sodium carbonate |
|---|---|---|---|
| 0 | 97.8 | 97.8 | 97.8 |
| 3 | 91.8 | 96 | 97.8 |
| 7 | 91.3 | 92.3 | 97.6 |
| 9 | — | — | 97.6 |

We claim:

1. A method for increasing the shelf life of at least one or more saturated liquid hydroxy- and alkoxyalkyl ketones which must be stored only as a liquid, which method comprises:

adding to said one or more ketones to be stored only as a liquid, from 0.0001 to 1% by weight of a base selected from the group consisting of tertiary amines, alkali metal hydroxides, alkali metal carbonates, alkali metal hydrogen carbonates, alkaline earth metal hydroxides, alkaline earth metal carbonates, alkaline earth metal hydrogen carbonates, and mixtures thereof.

2. A method for increasing the shelf life of liquid hydroxy- and alkoxyalkyl ketones as claimed in claim 1, wherein the hydroxyalkyl ketone employed is hydroxyacetone, 1-hydroxybutan-2-one or mixtures thereof.

3. A method as claimed in claim 1, wherein the alkoxyalkyl ketone is selected from the group consisting of methoxy-2-propanone, ethoxy-2-propanone, n-propoxy-2-propanone, isopropoxy-2-propanone, n-butoxy-2-propanone, isobutoxy-2-propanone, sec-butoxy-2-propanone, tert-butoxy-2-propanone, methoxy-2-butanone, ethoxy-2-butanone, n-propoxy-2-butanone, isopropoxy-2-butanone, n-butoxy-2-butanone, isobutoxy-2-butanone, sec-butoxy-2-butanone, tert-butoxy-2-butanone and mixtures thereof.

4. A method as claimed in claim 1, wherein the amount of base added is from 0.001 to 0.1% by weight.

5. A method as claimed in claim 1, wherein the amount of base added is from 0.005 to 0.05% by weight.

6. A method as claimed in claim 1, wherein the said added base is selected from the group consisting of tertiary amines, alkali metal carbonates, alkali metal hydroxides and mixtures thereof.

7. A method as claimed in claim 1, wherein the said added base is selected from the group consisting of tripropylamine, tributylamine, tetramethylhexanediamine and mixtures thereof.

8. A method as claimed in claim 1, wherein said added base is selected from the group consisting of sodium carbonate, sodium hydroxide, potassium carbonate, potassium hydroxide and mixtures thereof and is added to the liquid ketone to be stabilized in solid form or as an aqueous solution.

9. A liquid composition consisting essentially of at least one hydroxy- or alkoxyalkyl ketone having a purity of more than 97% and, as a stabilizer to increase its shelf life, at least one basic compound in a proportion of from 0.0001 to 1% by weight with reference to the total composition.

10. A liquid composition as claimed in claim 9, wherein said proportion of the base is from 0.0001 to 0.05% by weight.

11. A liquid composition as claimed in claim 9, wherein said proportion of the base is from 0.005 to 0.05% by weight.

12. A liquid composition as claimed in claim 9, wherein said base is selected from the group consisting of tertiary amines, alkali and alkaline earth metal hydroxides, alkali and alkaline earth metal carbonates, alkali and alkaline earth metal hydrogen carbonates and mixtures thereof.

13. A liquid composition as claimed in claim 12, wherein said proportion of the base is from 0.0001 to 0.05% by weight.

14. A liquid composition as claimed in claim 9, wherein said base is a tertiary alkyl mono- or diamine.

15. A liquid composition as claimed in claim 14, wherein said base is selected from the group consisting of tripropylamine, tributylamine, tetramethyl-hexanediamine and mixtures thereof.

16. A liquid composition as claimed in claim 13, wherein said base is tetramethylhexanediamine.

17. A liquid composition as claimed in claim 9, wherein said base is selected from the group consisting of sodium carbonate, sodium hydroxide, potassium carbonate, potassium hydroxide and mixtures thereof.

* * * * *